United States Patent
Laperle et al.

(10) Patent No.: US 11,987,780 B2
(45) Date of Patent: May 21, 2024

(54) L-GLASS: A NOVEL FUNCTIONALIZATION METHOD FOR COVALENTLY ATTACHING ECM PROTEIN TO OPTICAL GLASS

(71) Applicant: CEDARS-SINAI MEDICAL CENTER, Los Angeles, CA (US)

(72) Inventors: Alexander Laperle, North Hollywood, CA (US); Clive Svendsen, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1043 days.

(21) Appl. No.: 16/631,132

(22) PCT Filed: Jul. 13, 2018

(86) PCT No.: PCT/US2018/042173
§ 371 (c)(1),
(2) Date: Jan. 14, 2020

(87) PCT Pub. No.: WO2019/014644
PCT Pub. Date: Jan. 17, 2019

(65) Prior Publication Data
US 2020/0224140 A1     Jul. 16, 2020

Related U.S. Application Data

(60) Provisional application No. 62/532,873, filed on Jul. 14, 2017.

(51) Int. Cl.
*C12M 1/00*     (2006.01)
*C03C 17/30*    (2006.01)
(Continued)

(52) U.S. Cl.
CPC ............. *C12M 23/20* (2013.01); *C03C 17/30* (2013.01); *C03C 23/006* (2013.01); *C12M 3/00* (2013.01)

(58) Field of Classification Search
CPC ......... C12M 23/20; C12M 3/00; C03C 17/30; C03C 23/006
See application file for complete search history.

(56) References Cited

U.S. PATENT DOCUMENTS 5,077,210 A  * 12/1991  Eigler .................... C12N 11/06
                                                         436/527
6,191,255 B1 *  2/2001  Seiki .................... C12N 9/6491
                                                         435/325
(Continued)

FOREIGN PATENT DOCUMENTS

WO        2019014644 A1     1/2019

OTHER PUBLICATIONS

ISR and WO for PCT/US2018/042173 dated Sep. 10, 2018, 8 pages.
(Continued)

*Primary Examiner* — James M Mellott
(74) *Attorney, Agent, or Firm* — Nixon Peabody LLP (57) ABSTRACT

Described herein is functionalized glass allowing for robust attachment of extracellular matrix proteins (ECM) withstanding extended culturing periods. By first treating glass with a sulfur silane reagent, the treated glass can be activated via an amine-sulfur linker, after which ECM proteins are attached to the linker. The Inventors observed that this glass treatment combination (sulfur silane-linker-ECM) resisted degradation when compared to conventional surface coatings, such as poly-L-orthinine coated glass.

11 Claims, 13 Drawing Sheets

1. Plasma Oxygen Treatment

2. Thiol-Silane reaction

3. Sulfo-SMCC Treatment

3. NHS functionalized surface

NHS group will covalently bind to any primary amine (n-terminus and lys residues)

4. ECM protein coating (51) Int. Cl.
*C03C 23/00* (2006.01)
*C12M 3/00* (2006.01)

(56) References Cited

U.S. PATENT DOCUMENTS

| | | | |
|---|---|---|---|
| 6,824,866 B1 | 11/2004 | Glazer et al. | |
| 7,176,297 B2 | 2/2007 | Li et al. | |
| 2002/0094956 A1* | 7/2002 | Cosgrove | A61K 31/436 514/8.9 |
| 2006/0269983 A1* | 11/2006 | Cregger | C12Q 1/22 435/31 |
| 2008/0220982 A1 | 9/2008 | Vu | |
| 2010/0092384 A1 | 4/2010 | Bumb et al. | |
| 2011/0143967 A1 | 6/2011 | McGall et al. | |
| 2011/0294187 A1 | 12/2011 | Toner | |
| 2013/0277573 A1* | 10/2013 | Miller | H01J 37/20 427/595 |
| 2015/0005447 A1 | 1/2015 | Berti et al. | |
| 2016/0168523 A1 | 6/2016 | Glazier et al. | |

OTHER PUBLICATIONS

Seong, Microimmunoassay Using a Protein Chip: Optimizing Conditions for Protein Immobilization, Clin Diagn Lab Immunol., 2002, 9(4): 927-930.

Masuda et al., Coating extracellular matrix proteins on a (3-aminopropyl)triethoxysilane-treated glass substrate for improved cell culture, Biotechniques, 2014, vol. 56(4), pp. 172-179.

Rape et al., A synthetic hydrogel for the high-throughput study of cell-ECM interactions, Nat Commun., 2015, vol. 6 (8129), pp. 1-9.

Saha et al., Biomimetic interfacial interpenetrating polymer networks control neural stem cell behavior, J Biomed Mater Res A., 2007, vol. 81(1), pp. 240-249.

Saha et al., Substrate Modulus Directs Neural Stem Cell Behavior, Biophys J., 2008, vol. 95(9), pp. 4426-4438.

Regalado-Santiago et al., Mimicking Neural Stem Cell Niche by Biocompatible Substrates, Stem Cells In., 2016, pp. 1-15.

Saha et al., Designing synthetic materials to control stem cell phenotype, Curr Opin Chem Biol., 2007, vol. 11(4), pp. 381-387.

* cited by examiner

Day 40

L-Glass

PLO

Figure 4.

Day 50

L-Glass

PLO

Day 16

L-Glass

PLO

Figure 7.

Day 26

L-Glass

PLO

Figure 8.

Day 38 L-Glass / PLO

Figure 9. Day 38

L-GLASS: A NOVEL FUNCTIONALIZATION METHOD FOR COVALENTLY ATTACHING ECM PROTEIN TO OPTICAL GLASS

CROSS-REFERENCE TO RELATED APPLICATIONS

This application is the national phase of International Application No. PCT/US2018/042173, filed Jul. 13, 2018, which designated the U.S. and that International Application was published under PCT Article 21(2) in English. This application claims priority under 35 U.S.C. § 119(e) to U.S. Provisional Application No. 62/532,873, filed Jul. 14, 2017, the contents of which are herein incorporated by reference in their entirety.

FIELD OF THE INVENTION

Described herein is functionalized glass for use in cell culture, including glass treated to as to allow for robust attachment of extracellular matrix proteins.

BACKGROUND

Coating glass with extracellular matrix (ECM) proteins allows for study of cellular development in a complex, dynamic microenvironment. For example, to study developments of cellular features or localization of specific molecules by immunofluorescence staining, glass surfaces can used as a substrate as sufficiently thin and transparent to allow observation of cells.

Extracellular matrix (ECM) proteins such as collagen, fibronectin, and laminin are major components are known regulate cellular phenotypes, including stem cell development. For culturing cells, glass plates are often coated with ECM proteins that cells bind using adhesive transmembrane molecules. The effects of ECM molecules on cellular behavior are of great interest, including ECM-coated glass treated with silane reagents, to capture cellular dynamics. Silane reagents such as triethoxysilane are aminosilane compounds possessing free amino groups that can bind to free hydroxyl groups, such as those found on glass surfaces. When glass bonds with triethoxysilanes, the surface of the glass then presents amino groups that can bind to proteins. Despite these improvements, certain cellular development processes, such as neuron development, require multiple weeks of culturing (e.g., 7 weeks). These extended periods lead to significant degradation of the ECM proteins on the glass surface, even when using glass silane coating techniques.

Here, the Inventors developed an improved glass coating technique by first treating glass with a sulfur silane reagent. The treated glass is then activated via an amine-sulfur linker, after which ECM proteins are attached to the linker. The Inventors observed that this glass treatment combination (sulfur silane-linker-ECM) resisted degradation when compared to conventional surface coatings, such as poly-L-orthinine coated glass.

SUMMARY OF THE INVENTION

Described herein is a method of functionalizing optical glass, including treating optical glass with oxygen gas plasma, coating treated optical glass with a silane, and attaching a linker to the coated and treated optical glass. In other embodiments, the coated and treated optical glass with a linker is attached to one or more extracellular matrix proteins. In other embodiments, the one or more extracellular matrix proteins includes a laminin, a fibronectin, and/or a collagen. In other embodiments, the coated and treated optical glass with a linker is attached to an integrin. In other embodiments, the linker includes sulfo-SMCC. In other embodiments, the silane includes a thiol-silane. In other embodiments, the thiol-silane includes (3-Mercaptopropyl) trimethoxysilane. In other embodiments, the glass is washed in acid prior to treatment. In other embodiments, the optical glass includes a coverslip. Also described herein is a cell culture vessel functionalized by the aforementioned method.

Described herein is a method of extended cell culturing on functionalized glass, including seeding a quantity of cells on a cell culture vessel including functionalized glass, and culturing the cells, wherein extended cell culturing is for at least 25 days. In other embodiments, the extended cell culturing is for at least 35 days. In other embodiments, the extended cell culturing for at least 50 days. In other embodiments, the functionalized glass includes one or more extracellular matrix proteins attached to a linker including sulfo-SMCC, the linker attached to (3-Mercaptopropyl) trimethoxysilane. In other embodiments, the one or more extracellular matrix proteins include a laminin, a fibronectin, and/or a collagen. In other embodiments, the functionalized glass includes an integrin attached to a linker including sulfo-SMCC, the linker attached to (3-Mercaptopropyl) trimethoxysilane.

Further described herein is a cell culture vessel including functionalized glass, wherein the functionalized glass includes a silane and a linker. In other embodiments, the functionalized glass includes one or more extracellular matrix proteins. In other embodiments, the silane includes (3-Mercaptopropyl) trimethoxysilane, and the linker includes sulfo-SMCC.

As described, current techniques for attaching cells to extracellular matrix (ECM) proteins to glass involve use of silanes, siloxanes, PLO or PLI to add a charge to the glass surface and promote electrostatic adsorption of the ECM proteins. Such processes are effective for short-term culturing, but under prolonged culturing periods, leads to clumping and detachment of cultured cells. For example, current practice using PLO can lead to over half of samples becoming rendered unusable over the course of any given experiment. Specialized plastic coverslips possessing a charge similar to TCPS have been developed, but such materials are not optically clear and unsuitable for cellular studies. Plastic surface also exhibit autofluoresence in the 488 nm wavelength that precludes use of immunolabeling techniques.

Described herein is a method of functionalizing optical glass, including treating optical glass with oxygen gas plasma, coating treated optical glass with a silane, and attaching a linker to the coated and treated optical glass. In other embodiments, the coated and treated optical glass with a linker is attached to one or more extracellular matrix proteins. In various embodiments, the one or more extracelluar matrix (ECM) protein includes a laminin, a fibronectin, a collagen, a proteoglycan, an elastin, a heparan sulfate, and/or a glycoprotein. In other embodiments, the one or more extracellular matrix proteins includes a laminin, a fibronectin, and/or a collagen. In other embodiments, the one or more extracellular matrix proteins includes matrigel. In other embodiments, the coated and treated optical glass with a linker is attached to an integrin. In other embodiments, the linker includes sulfo-SMCC. In other embodiments, the silane includes a thiol-silane. In other embodiments, the thiol-silane includes (3-Mercaptopropyl) trimethoxysilane. In other embodiments, the glass is washed in acid prior to treatment. In other embodiments, the optical glass includes a coverslip.

Also described herein is a cell culture vessel functionalized by a method of functionalizing optical glass, including treating optical glass with oxygen gas plasma, coating treated optical glass with a silane, and attaching a linker to the coated and treated optical glass. In other embodiments, the coated and treated optical glass with a linker is attached to one or more extracellular matrix proteins. In various embodiments, the one or more extracelluar matrix (ECM) protein includes a laminin, a fibronectin, a collagen, a proteoglycan, an elastin, a heparan sulfate, and/or a glycoprotein. In other embodiments, the one or more extracellular matrix proteins includes a laminin, a fibronectin, and/or a collagen. In other embodiments, the one or more extracellular matrix proteins includes matrigel. In other embodiments, the coated and treated optical glass with a linker is attached to an integrin. In other embodiments, the linker includes sulfo-SMCC. In other embodiments, the silane includes a thiol-silane. In other embodiments, the thiol-silane includes (3-Mercaptopropyl) trimethoxysilane. In other embodiments, the glass is washed in acid prior to treatment. In other embodiments, the optical glass includes a coverslip.

Described herein is a method of extended cell culturing on functionalized glass, including seeding a quantity of cells on a cell culture vessel including functionalized glass, and culturing the cells, wherein extended cell culturing is for at least 25 days. In other embodiments, the extended cell culturing is for at least 35 days. In other embodiments, the extended cell culturing for at least 50 days. In other embodiments, the extended cell culturing is for at least 25-35 days, at least 35-50 days or 50 days or more. In various embodiments, the cultured cells are neurons. In other embodiments, the functionalized glass includes one or more extracellular matrix proteins attached to a linker including sulfo-SMCC, the linker attached to (3-Mercaptopropyl) trimethoxysilane. In other embodiments, the one or more extracellular matrix proteins include a laminin, a fibronectin, and/or a collagen. In other embodiments, the one or more extracellular matrix proteins includes matrigel. In other embodiments, the functionalized glass includes an integrin attached to a linker including sulfo-SMCC, the linker attached to (3-Mercaptopropyl) trimethoxysilane.

Further described herein is a cell culture vessel including functionalized glass, wherein the functionalized glass includes a silane and a linker. In other embodiments, the functionalized glass includes one or more extracellular matrix proteins. In other embodiments, the silane includes (3-Mercaptopropyl) trimethoxysilane, and the linker includes sulfo-SMCC.

EXAMPLE 1

Generally

Figure 1:
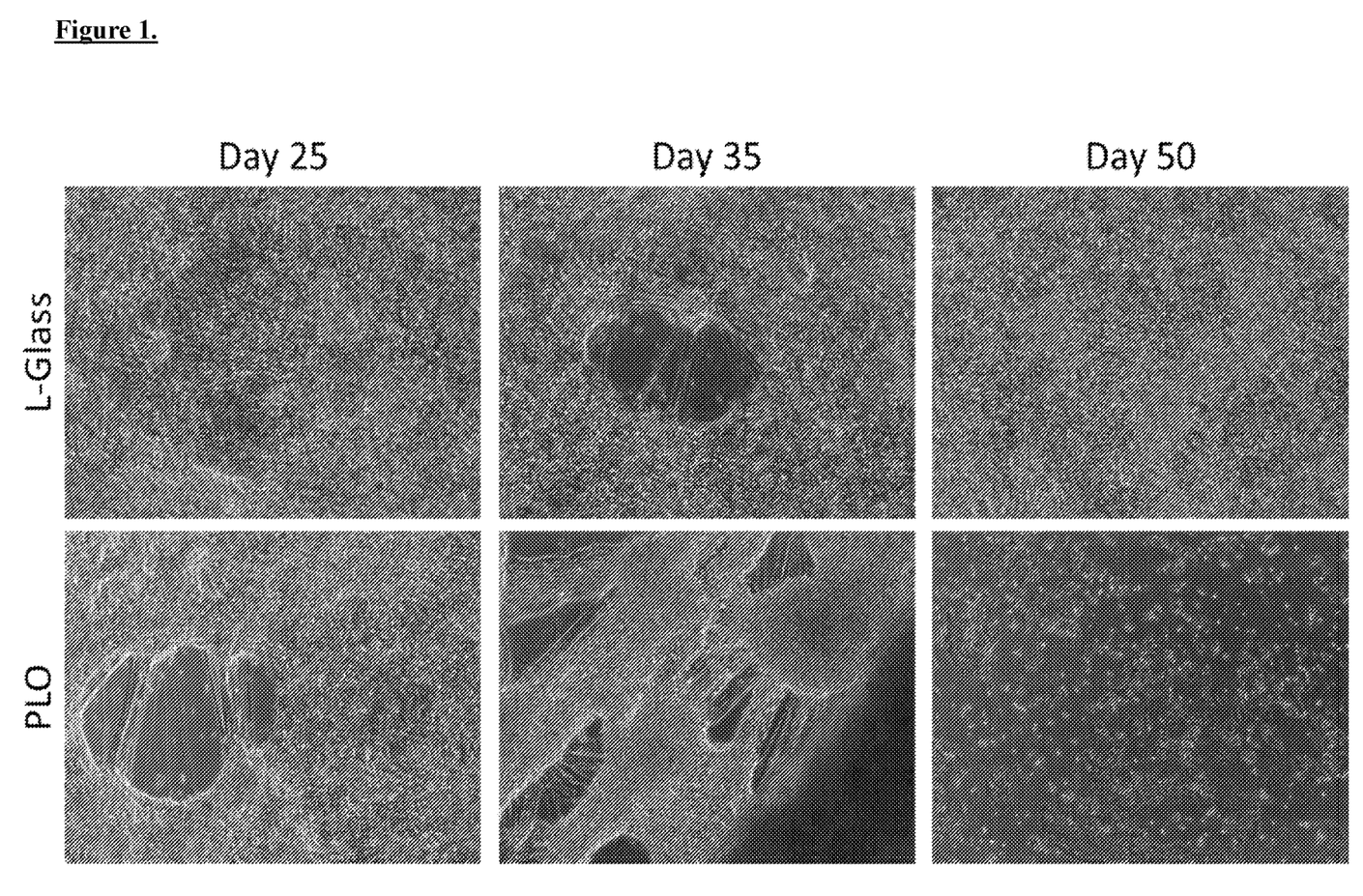
FIG. 1. Culture of iPSC derived dopaminergic neurons on L-Glass and PLO coated glass results in similar short term attachment and growth of neurons (to D25). By day 35 of culture the neurons on PLO coated glass have fully clumped and largely detached from the substrate while the same cells on L-Glass are attached and viable past day 50 of culture.
Figure 12:
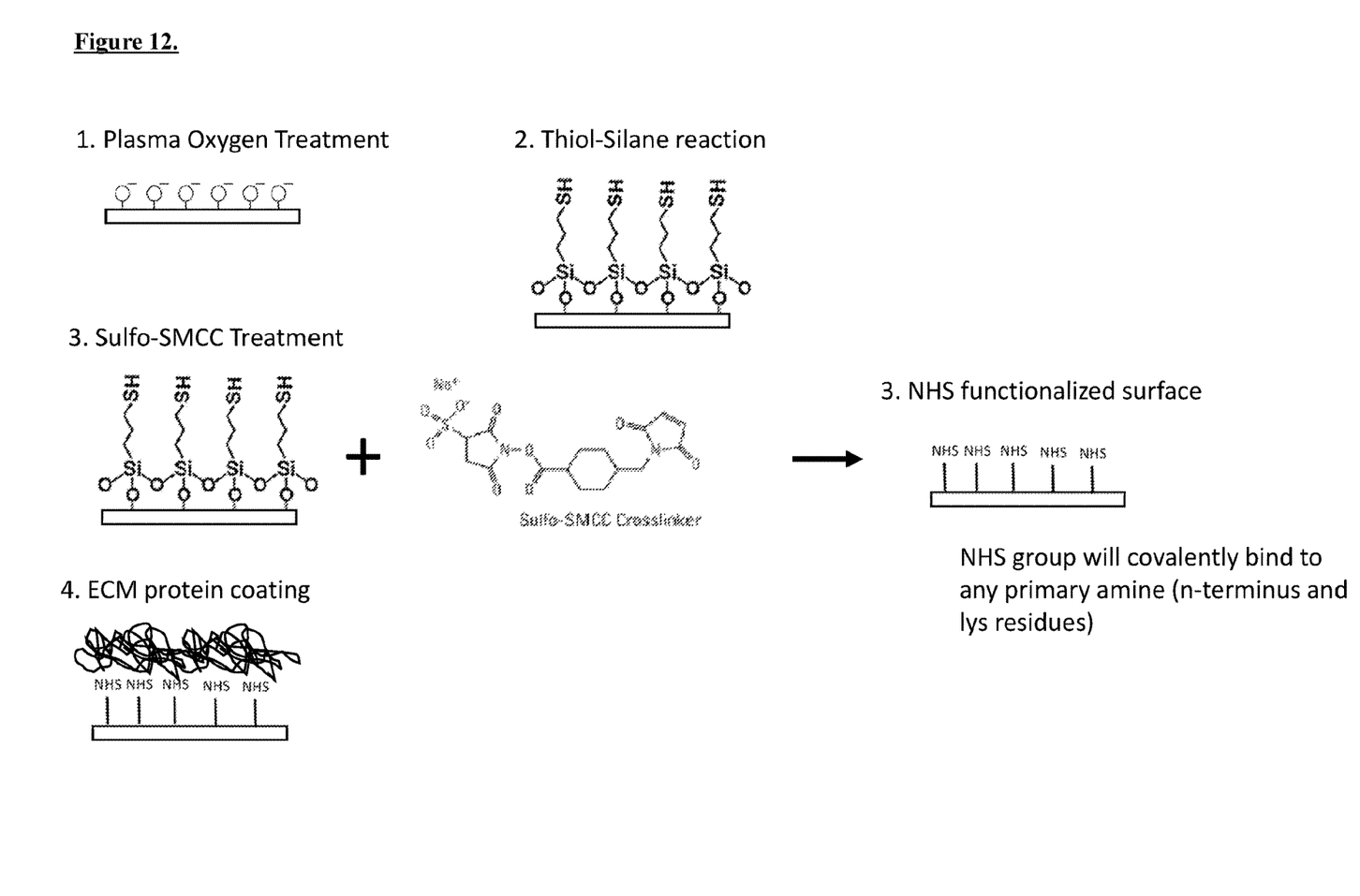
FIG. 12. L-glass surface process.

Briefly, the Inventors' newly developed techniques involve a series of preparation and coating steps. For example, a 5-step method is as follows:
1. Acid wash glass coverslips to remove organic contaminantes
2. Oxygen gas plasma treatment
3. Thiol-silence treatment
4. Sulfo-SMCC reaction
5. ECM protein coating The aforementioned process creates a permanent covalent bond between any ECM protein and any glass substrate. Process is illustrated in FIG. 12 and exemplary results of superior adherence and culture integrity shown in FIG. 1.

EXAMPLE 2

Materials Required

More specifically, a detailed protocol is outlined:
Thiolsilane Reagent: (3-Mercaptopropyl) trimethoxysilane (Sigma Product No. 175617-25G)
Acetone: solvent/diluent for Thiolsilane Reagent
Coupling Buffer: PBS-EDTA (50 mM Phosphate, 0.15 M NaCl, 5 mM EDTA, pH 7.2). Sterile PBS add EDTA to a concentration of 5 mM (1.46 g EDTA/L PBS). Alternatively, other neutral or slightly alkaline amine-free buffers such as borate, HEPES, and bicarbonate also may be used. Whatever buffer is chosen, include 5-10 mM EDTA to prevent metal-catalyzed oxidation of sulfhydryls during the final cross-linking step. Also, avoid sulfhydryl-containing components in the buffer, as these will react with the maleimide portion of the crosslinker and inhibit conjugation of the ECM.
Crosslinker: Sulfo-SMCC (Product No. 22322)
Prior to starting—Acid wash glass coverslips overnight in 2M HCL at RT
Section 1: Thiolsilylate the Glass Surface—Place coverslips in a glass container. Plastic will dissolve 1. Thoroughly wash and dry the glass surface to be coated. Note: Perform Section 1 steps 3 and 4 in a fume hood.
2. Oxygen Plasma treat cleaned/dried coverslips. 100 W for 1 min—standard recipe #2
3. Prepare a 2% solution of the Thiolsilane Reagent (3-Mercaptopropyl) trimethoxysilane) in acetone (400 uL thiolsilane and 19.6 mL acetone). Prepare a volume sufficient to immerse or cover the surface material.
4. Immerse surface in the diluted reagent for 5 mins.
5. Rinse surface 2× with dry acetone.
6. Allow surface to air-dry. Note: The dried silylated surface may be stored for later use.

Section 2: Activate Thiolsilylated surface
1. Add 2 mg Crosslinker (Sulfo-SMCC) to 10 ml Coupling Buffer. This solution may be scaled as needed, and must be used immediately to avoid hydrolysis.
2. Cover silylated surface with the Crosslinker solution.
3. Incubate for 1 hour at room temperature (RT).
4. Rinse the modified surface with Coupling Buffer. Note: The activated surface may be dried and stored desiccated at 4° C. for later use.

Section 3: Cross-Link ECM to Activated Surface
1. Cover the surface material with the ECM coating solution. The solution may be diluted in sterile PBS to a volume sufficient to cover the surface material. For optimal results, ensure that the final protein concentration is greater than 10 μg/ml.
2. Incubate for a minimum of 2 hours at 37 C (overnight preferable)
3. Remove the ECM solution
4. Thoroughly rinse the surface with sterile PBS to ensure that only covalently attached ECM protein remains.
5. The surface is now ready to use for cell culture and other applications. Depending on stability of the particular protein, the surface material may be dried for storage.

EXAMPLE 3

Comparison of L-Glass and Conventional Substrates

In this study, iPSC derived dopamine neurons were observed for 50 days on 2 substrates: (1) PLO—classic method—electrostatic adsorption of coating protein, (2) L-glass—covalent binding of coating protein to glass. For both substrates, the same extracellular matrix (ECM) coating protein, matrigel, was utilized. Immunostaining included TH—tyrosine hydroxylase, a marker for dopaminergic neurons and MAP2ab—neurofilament protein—a marker for neurons.

Figures 2, 2A:
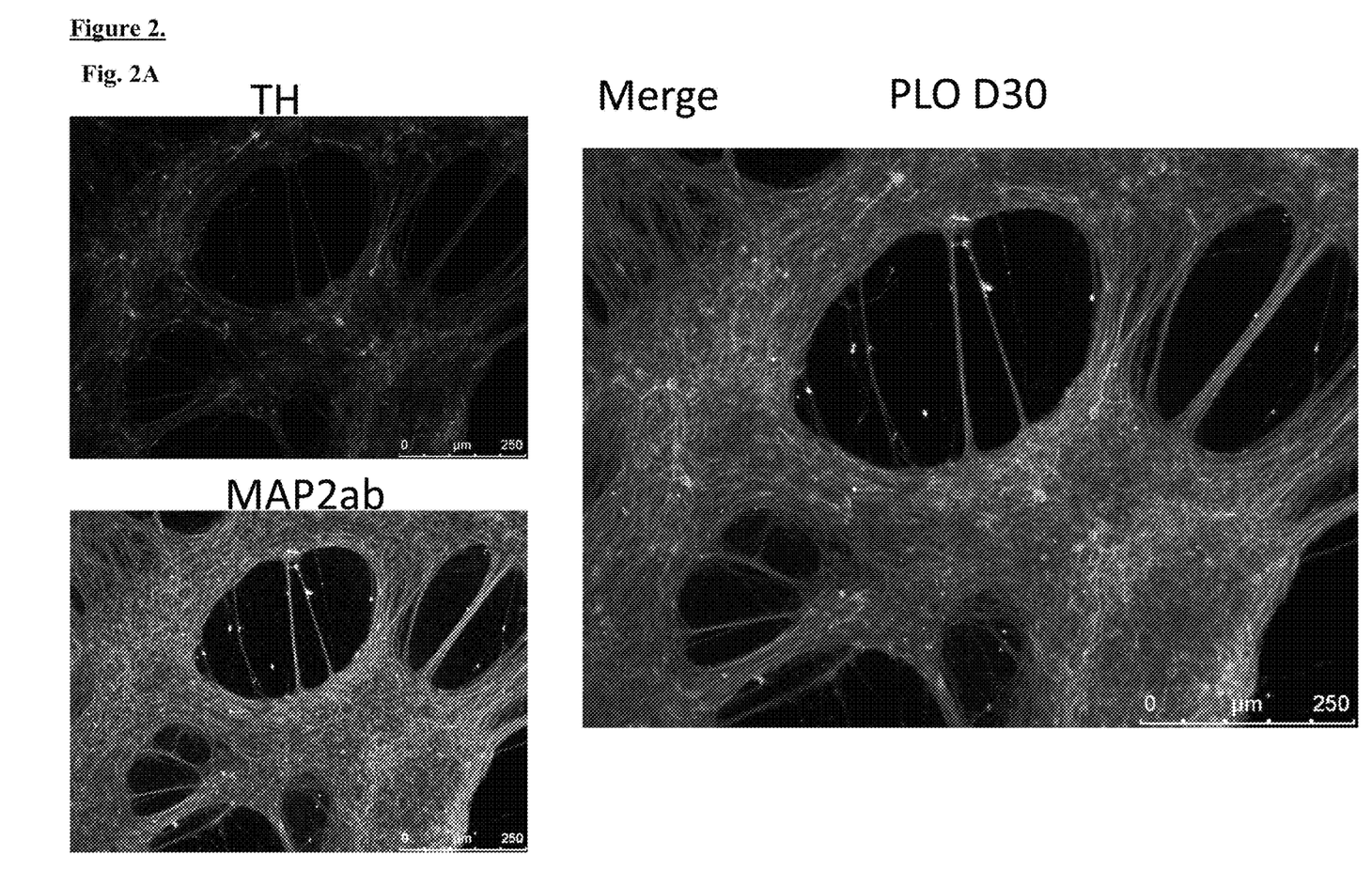
FIG. 2. Day 30 results.
As shown in FIG. 2A, D30 lifting/clumping of neurons.
Figures 2, 2B:
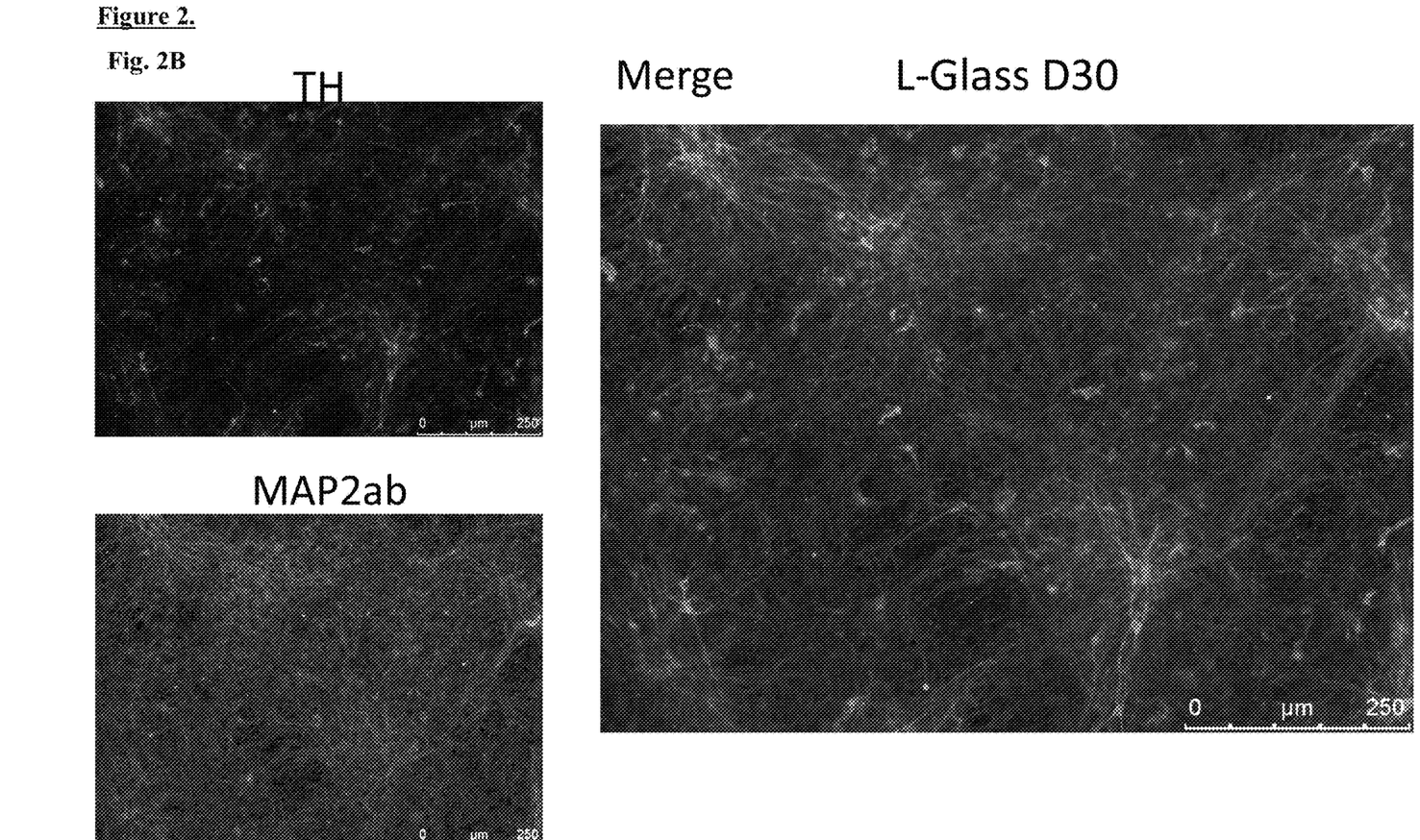
IN FIG. 2B, D30 neurons maintain spread morphology on matrigel ECM coating.
Figure 3:
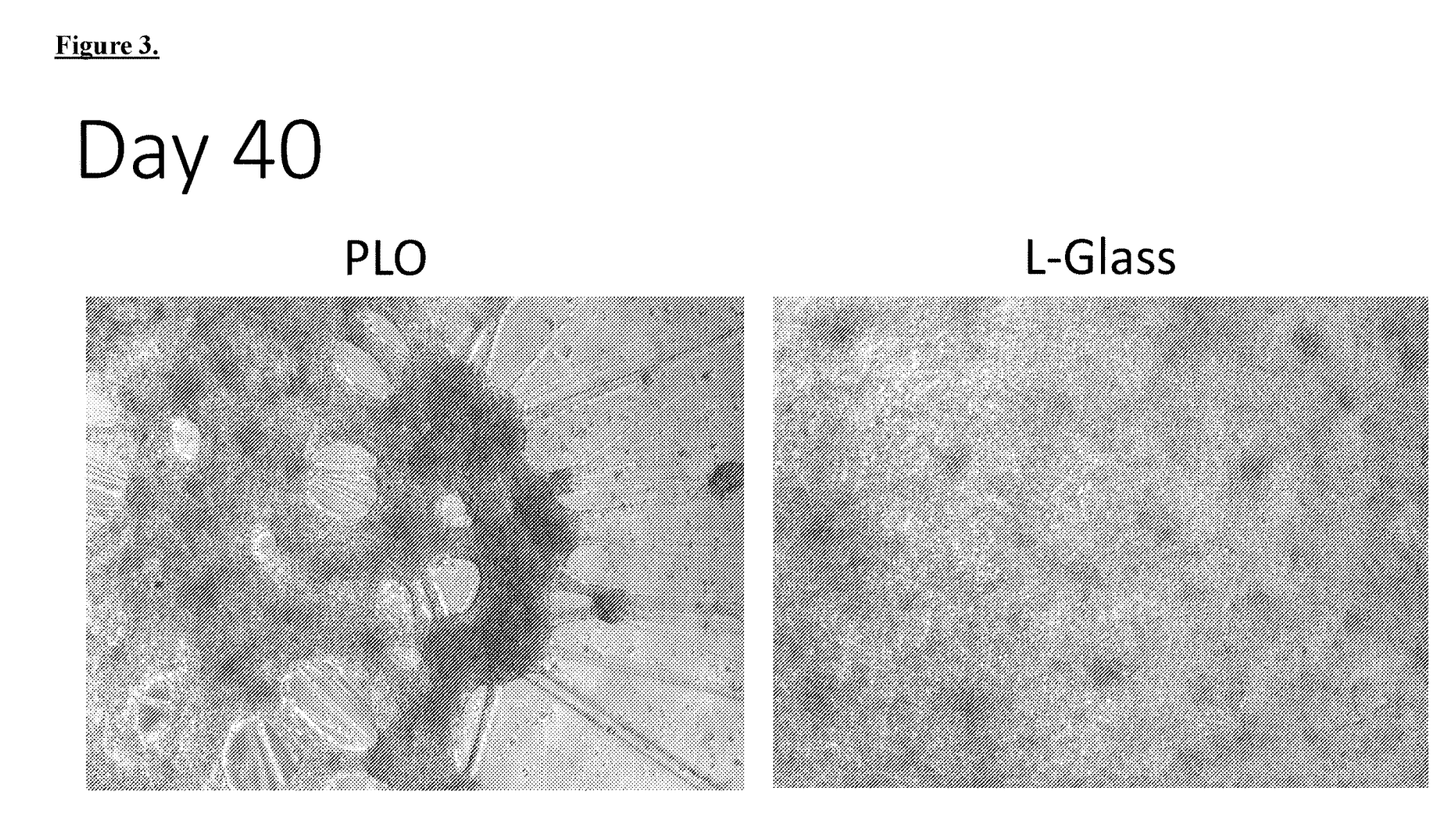
FIG. 3. Day 40 results. PLO neurons heavily clumped and largely detached from substrate.
Figure 4:
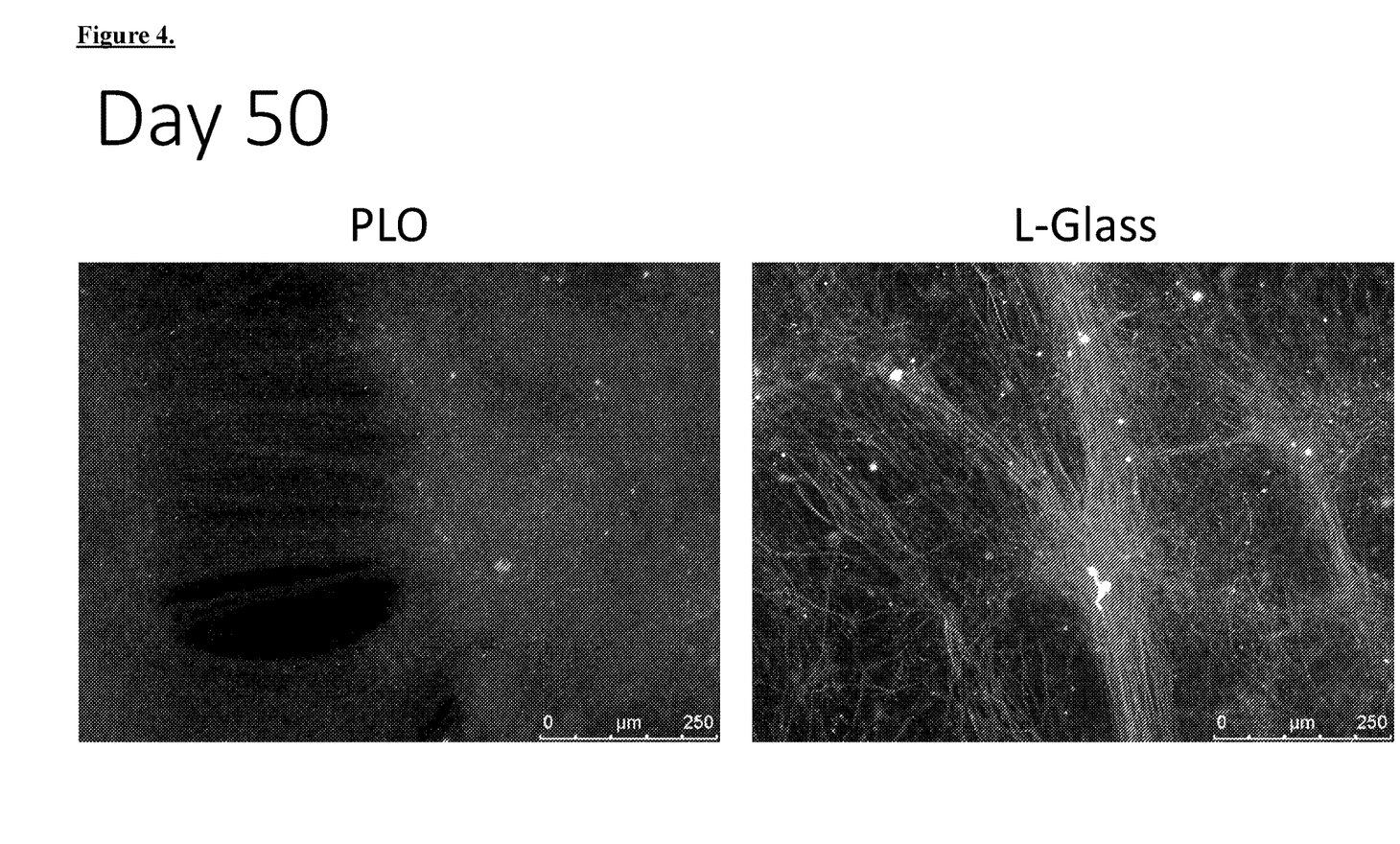
FIG. 4. Day 50 results. Detached PLO cells by D50, loss of TH staining. Note the remarkable difference in staining and appearance of fine neural processes on L-glass cultured cells.
Figure 5:
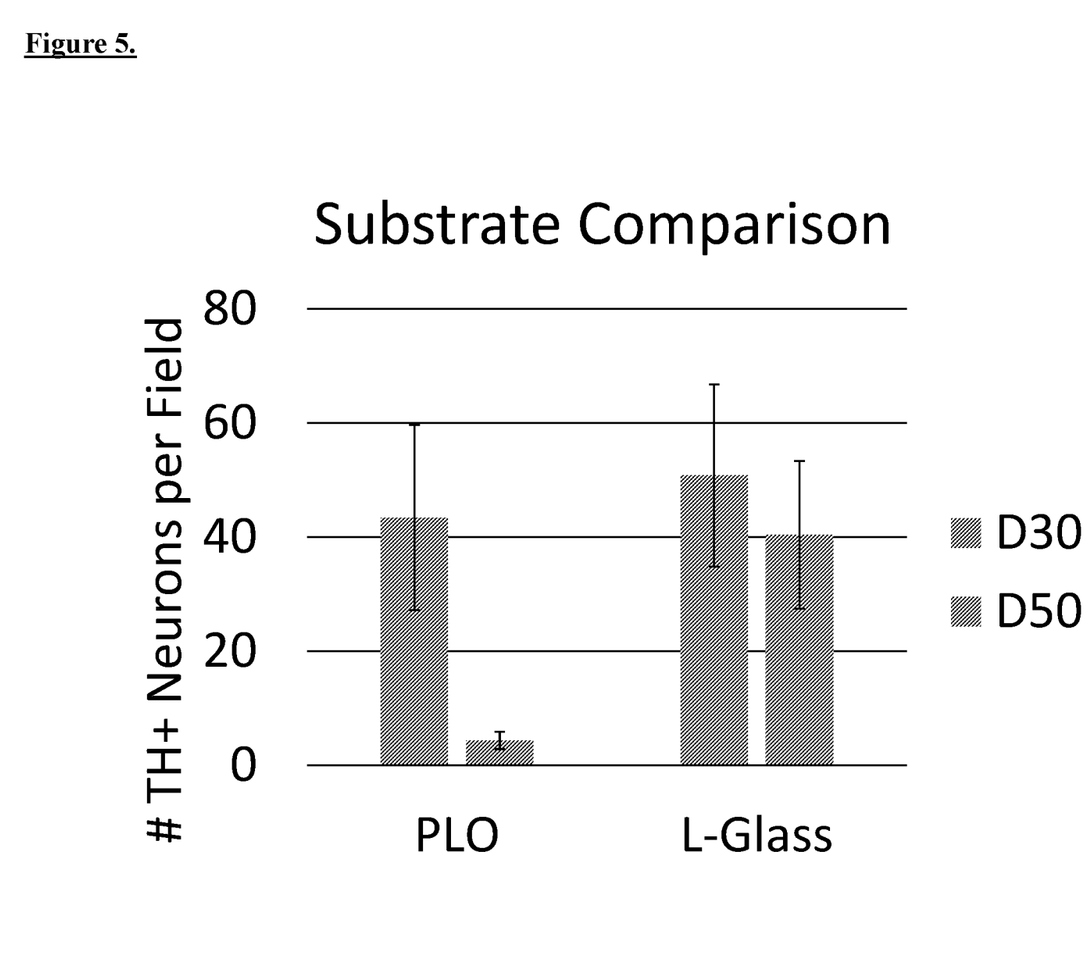
FIG. 5. Cell Counts on matrigel for TH. Counts of TH+ neurons per field, 5 fields per condition analyzed.

As shown in FIG. 2, at day 30, conventional PLO results in degradation of substrate and lifting/clumping of neurons after extended culturing, whereas L-glass substrate maintains integrity, allowing for more consistent differentiation in the culture. As shown in FIG. 3, day 40 PLO cultures are virtually unusable as largely detached, in contrast to the attached cultures on L-glass. As shown in FIG. 4, by day 50, the PLO cultured cells are detached with loss of TH staining, but cells cultured on L-glass maintain integrity with TH expression. Increase of TH+ cells in L-glass cultures were confirmed by cell counts as shown in FIG. 5.

EXAMPLE 4

Comparison of L-Glass and Conventional Substrates

In this study, iPSC derived motor neurons (diMN) were observed for 38 days on 2 substrates (1) PLO—classic method—electrostatic adsorption of coating protein, (2) L-glass—covalent binding of coating protein to glass. For both substrates, the same ECM coating protein, laminin, was utilized.

D12 motor neurons were thawed and plated onto PLO and L-glass coated coverslips. Immunostaining included SMI32—neurofilament protein associated with motor neurons and ISL1—transcription factor—marker for motor neurons when co-expressed with SMI32.

Figure 6:
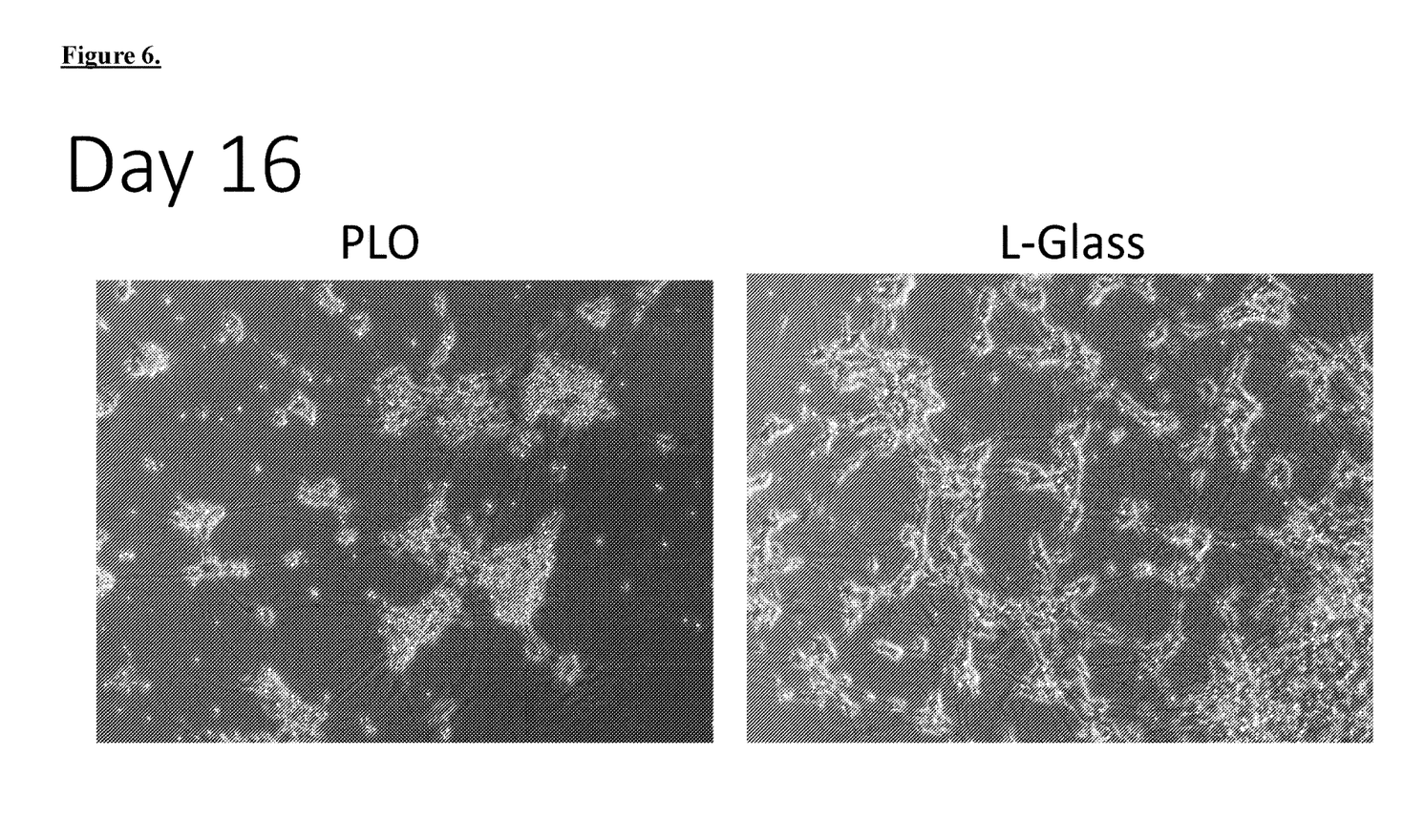
FIG. 6. Day 16 motor neuron differentiation. Differentiated motor neurons shown. 4 days post plating, note more extensive neural processes on L-glass, both using lamining ECM coating.
Figure 7:
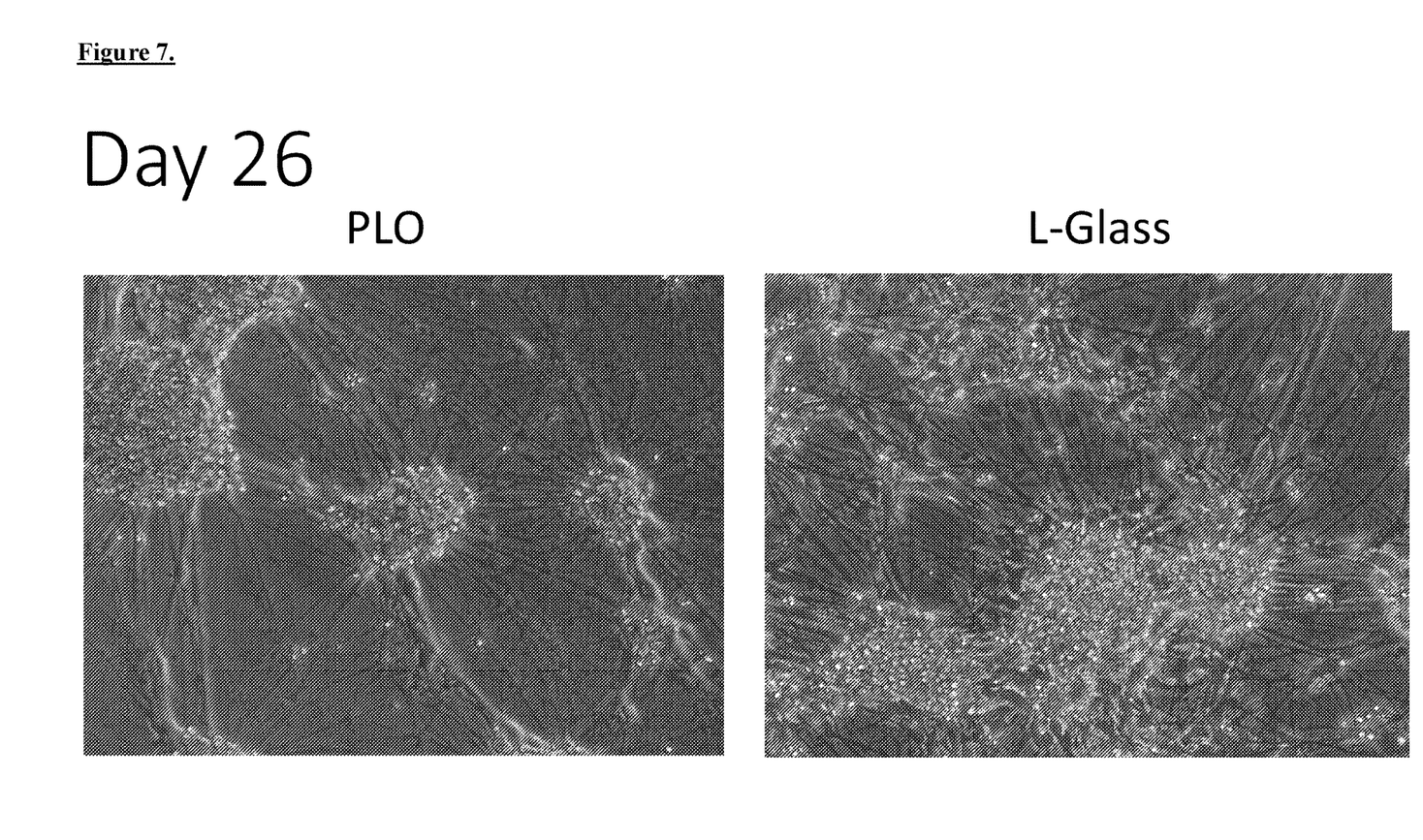
FIG. 7. Day 26 motor neuron differentiation. Much greater clumping is visible on PLO, less extensive on L-glass.
Figure 8:
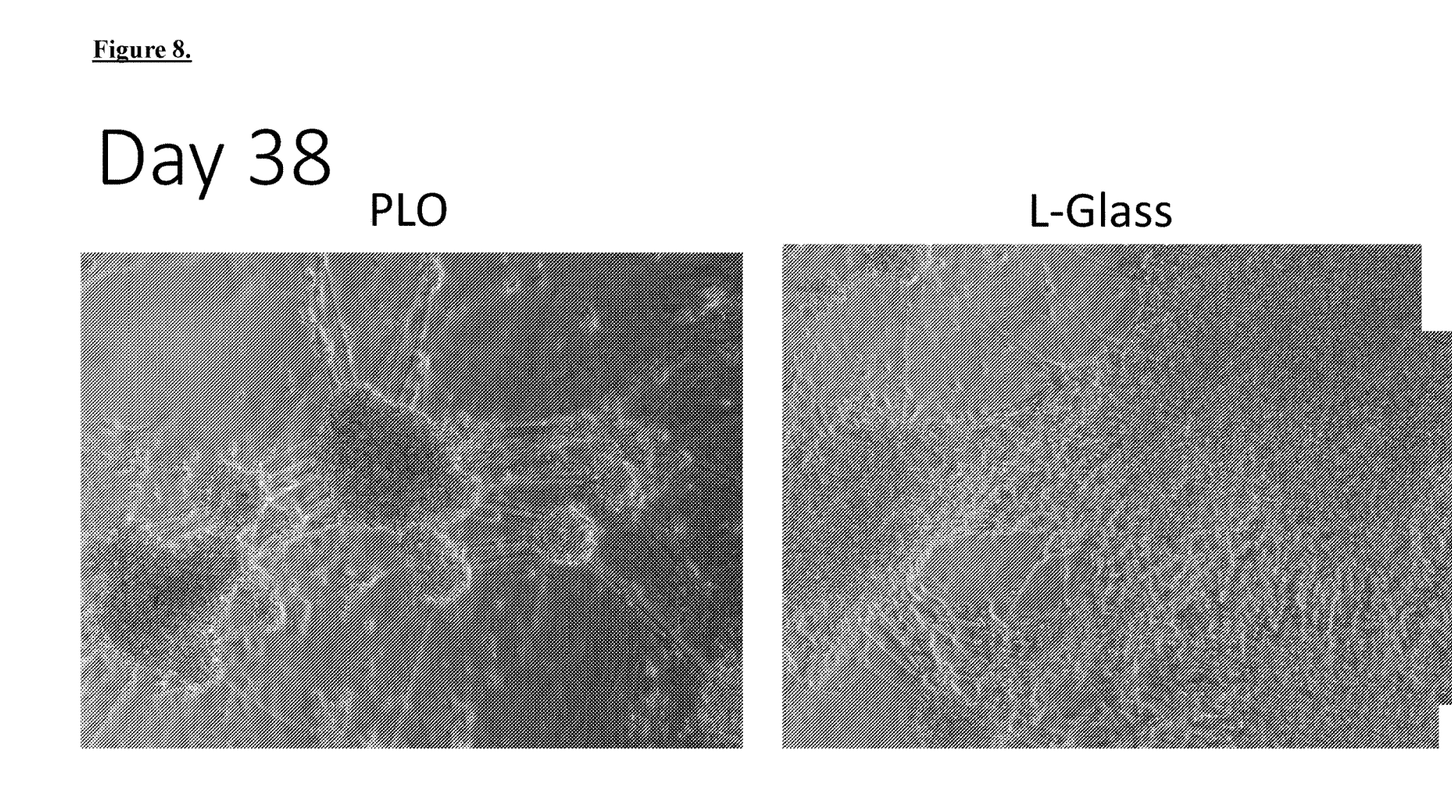
FIG. 8. Day 38 Heavy clumping on PLO substrate. Under longer term culturing, PLO samples are virtually unstable.
Figure 9:
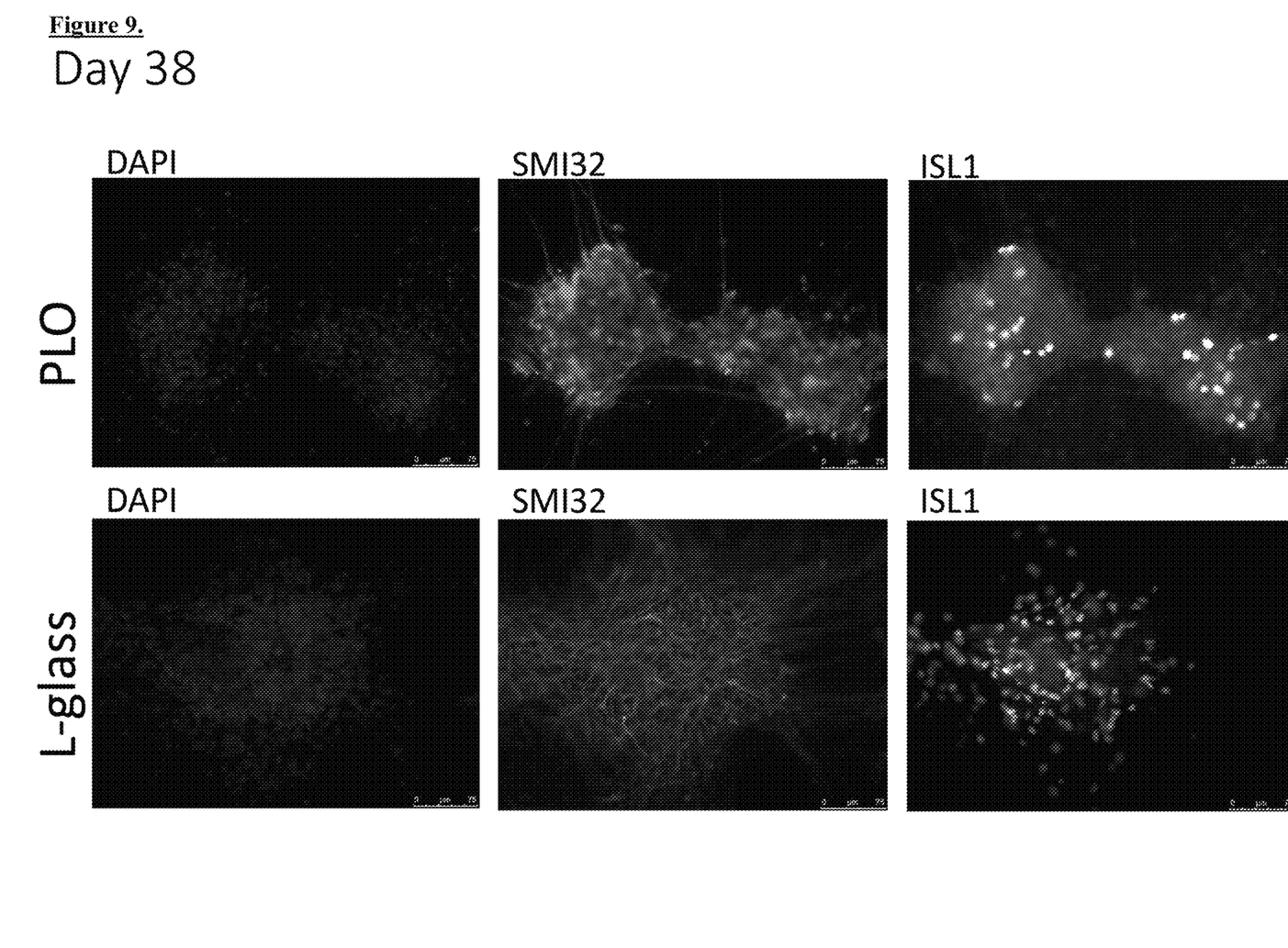
FIG. 9. Day 38 Staining of cell markers. Markers include DAPI, SMI32 and ISL1. Again, remarkable difference in staining and appearance of fine neural processes on L-glass cultured cells.
Figure 10:
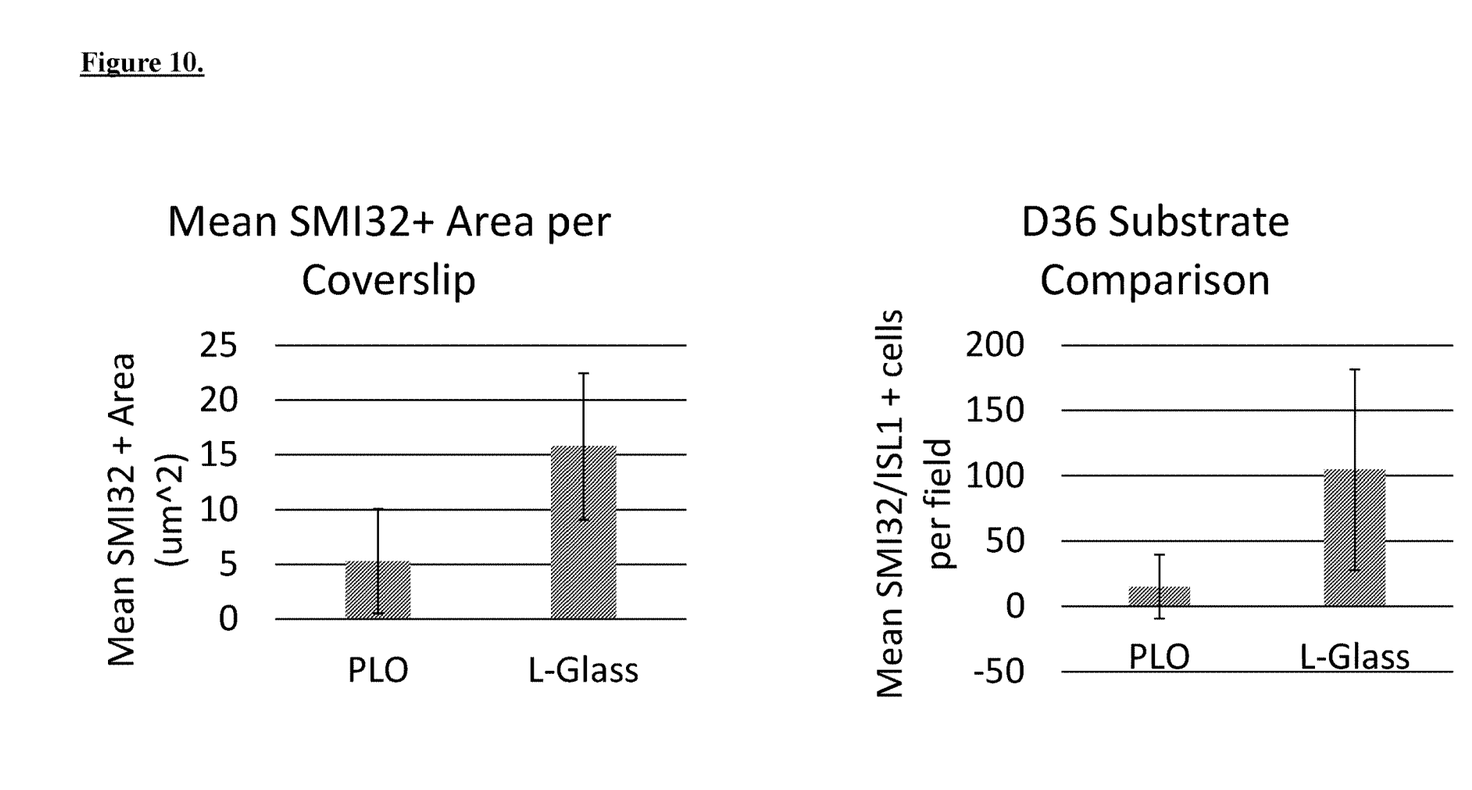
FIG. 10. Cell Counts on lamining for SMI32 and ISL1. More cells stay attached and spread on L-glass. Counts of dual positive cells per field, 5 fields per condition analyzed.

Here, laminin as ECM coating protein was utilized in conjunction with other markers of neuronal differentiation. As shown in FIG. 6, differentiation is clearly enhanced on L-glass as shown by the more extensive neural processes by day 16. As shown in FIG. 7, a greater amount of cell detachment and clumping is visible on PLO after 26 days. As shown in FIG. 8, PLO cultures are virtually unusable on PLO, with heavy clumping and cellular detachment. Staining is clearly improved in L-glass samples on day 38, as shown in FIG. 9. Increase of SMI32 and ISL+ cells in L-glass cultures were confirmed by cell counts as shown in FIG. 10.

EXAMPLE 5

Robust Storage Capability

Figure 11:
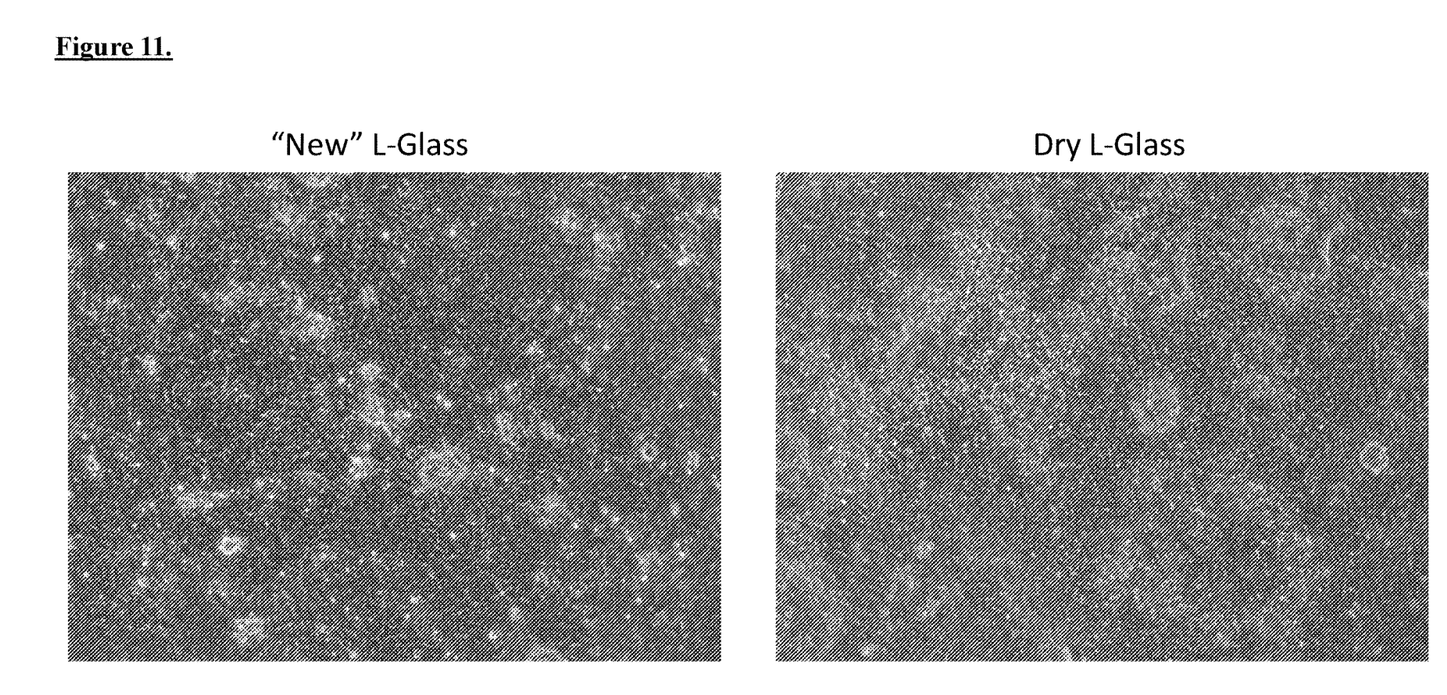
FIG. 11. Comparison of L-glass storage. Cells maintain excellent viability even when cultured on glass stored for 21 days.

For these studies, dry L-Glass coverslips were matrigel coated overnight, washed with PBS, and stored dry at RT for 21 days prior to seeding cells. New L-glass coverslips were Matrigel coated overnight prior to seeding cells. As shown in FIG. 11, performance of both types of fabricated L-glass performed well, without cell detachment, thereby demonstrating long-term storage capability of L-glass treated materials.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are glass coating techniques, including use of silanes, siloxanes, and functional linkers associated therewith, further including techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of functionalizing optical glass, comprising:
   treating optical glass with oxygen gas plasma;
   coating the treated optical glass with a silane; and
   attaching a linker to the coated and treated optical glass, wherein the attached linker is attached to one or more extracellular matrix proteins.

2. The method of claim 1, wherein the one or more extracellular matrix proteins comprise a laminin, a fibronectin, and/or a collagen.

3. The method of claim 2, wherein the linker comprises sulfosuccinimidyl 4-(N-maleimidomethyl)cyclohexane-1-carboxylate (sulfo-SMCC).

4. The method of claim 1, wherein the linker comprises sulfosuccinimidyl 4-(N-maleimidomethyl)cyclohexane-1-carboxylate (sulfo-SMCC).

5. The method of claim 1, wherein the silane comprises a thiol-silane.

6. The method of claim 5, wherein the thiol-silane comprises (3-Mercaptopropyl) trimethoxysilane.

7. The method of claim 1, further comprising washing the glass in acid prior to treatment of the optical glass with oxygen gas plasma.

8. The method of claim 1, wherein the optical glass comprises a coverslip.

9. The method of claim 1, wherein the one or more extracellular matrix proteins comprise a laminin and/or fibronectin.

10. The method of claim 9, wherein the linker comprises an amine-sulfur linker.

11. A cell culture vessel functionalized by the method of claim 1.

* * * * *